US012727792B2

(12) United States Patent
Dai et al.

(10) Patent No.: US 12,727,792 B2
(45) Date of Patent: Sep. 8, 2026

(54) NON-INVASIVE BLOOD GLUCOSE MONITORING DEVICE AND MANUFACTURING METHOD THEREOF

(71) Applicant: Taiwan-Asia Semiconductor Corporation, Hsinchu City (TW)

(72) Inventors: Shu-Wen Dai, Hsinchu City (TW); Fu-Yung Tsai, Hsinchu City (TW); Chuan-Fa Lin, Hsinchu City (TW)

(73) Assignee: TAIWAN-ASIA SEMICONDUCTOR CORPORATION, Hsinchu City (TW)

(*) Notice: Subject to any disclaimer, the term of this patent is extended or adjusted under 35 U.S.C. 154(b) by 162 days.

(21) Appl. No.: 18/767,060

(22) Filed: Jul. 9, 2024

(65) Prior Publication Data

US 2025/0120617 A1 Apr. 17, 2025

(30) Foreign Application Priority Data

Oct. 12, 2023 (TW) ................................ 112139042

(51) Int. Cl.
*A61B 5/145* (2006.01)

(52) U.S. Cl.
CPC ...... *A61B 5/14532* (2013.01); *A61B 2562/12* (2013.01)

(58) Field of Classification Search
None
See application file for complete search history.

(56) References Cited

U.S. PATENT DOCUMENTS 6,952,603 B2 * 10/2005 Gerber ............... A61B 5/14532 356/478
8,764,653 B2 7/2014 Kaminska et al.
11,990,557 B2 * 5/2024 Shen ..................... H10F 55/165
12,230,618 B2 * 2/2025 Hasegawa ............ H10W 90/00
(Continued)

FOREIGN PATENT DOCUMENTS

EP 3892194 A1 10/2021
WO 2018223090 A1 12/2018

OTHER PUBLICATIONS

Annotated amendment from EP 24175648, 3 pages. (Year: 2025).*

*Primary Examiner* — Michael Fuelling
(74) *Attorney, Agent, or Firm* — MUNCY, GEISSLER, OLDS & LOWE, P.C.

(57) ABSTRACT

The invention provides a manufacturing method for a non-invasive blood glucose monitoring device, which comprises the following steps: providing a substrate; performing an injection molding process or an electroplating process, to form at least one light-blocking wall on the substrate, wherein each light-blocking wall includes a lower wall-structure and an upper wall-structure, and the lower wall-structure connects the substrate and the upper wall-structure connects the lower wall-structure; arranging a light-emitting element and a light-receiving element on the substrate and separating the light-emitting element and the light-receiving element by the at least one light-blocking wall; forming a packaging structure on the substrate in which the light-emitting element and the light-receiving element are packaged; and disposing a transparent cover on the packaging structure and the at least one light-blocking wall and limiting the transparent cover to a configuration height by the at least one light-blocking wall.

8 Claims, 3 Drawing Sheets

(56) References Cited

U.S. PATENT DOCUMENTS

| | | | | |
|---|---|---|---|---|
| 2002/0161286 | A1 | 10/2002 | Gerber et al. | |
| 2015/0190079 | A1* | 7/2015 | Yamaji | A61B 5/14552 29/841 |
| 2021/0282673 | A1* | 9/2021 | Petcavich | A61B 5/0295 |
| 2022/0140173 | A1 | 5/2022 | Shen et al. | |
| 2023/0059535 | A1 | 2/2023 | Tsou et al. | |
| 2023/0062342 | A1 | 3/2023 | Halac et al. | |
| 2023/0301553 | A1 | 9/2023 | Rong et al. | |

* cited by examiner

NON-INVASIVE BLOOD GLUCOSE MONITORING DEVICE AND MANUFACTURING METHOD THEREOF

CROSS REFERENCE TO RELATED APPLICATION

This application claims the benefit of Taiwan Patent Application Serial No. 112139042 filed on Oct. 12, 2023. The entirety of each Application is incorporated herein by reference.

BACKGROUND OF THE INVENTION

1. Field of the Invention

The present invention relates to a non-invasive blood glucose monitoring device and a manufacturing method thereof, especially a non-invasive blood glucose monitoring device and a manufacturing method thereof by improving a conventional dispensing way for forming light-blocking walls.

2. Description of Related Art

In conventional manufacturing steps of a non-invasive blood glucose monitoring device, a light-emitting element and a light-receiving element on a substrate are first packaged through a packaging material, and then a cover is disposed on the packaging material. Next, grooves are formed at appropriate locations of the cover and the packaging material (such as between the light-emitting element and the light-receiving element and/or around the light-emitting element and the light-receiving element) by half-cutting, and at last the grooves are filled with an opaque glue material by dispensing, so that light-blocking walls form after the opaque glue material being solidified.

However, since the conventional manufacturing steps for forming light-blocking walls are relatively complex and can only be applied for small area devices, which increases manufacturing cost and affects the manufacturing accuracy. Furthermore, in the half-cutting step of the cover and the packaging material, limited by sizes of cutting tools, the light-blocking wall is formed with a width larger than 200 μm, which is difficult to be further reduced. In addition, for the light-blocking wall formed by dispensing, because of uncontrollable uniformity or a few bubbles thereof, it is very likely to decrease the light-blocking rate of the light-blocking wall, so as to affect the accuracy of blood glucose monitoring.

In light of this, it is really worthy of research and development, for solving those above-mentioned problems, to design a manufacturing method for a non-invasive blood glucose monitoring device.

SUMMARY OF THE INVENTION

An objective of the present invention is to provide a manufacturing method for a non-invasive blood glucose monitoring device by improving conventional dispensing way for forming light-blocking walls.

Another objective of the present invention is to provide a manufacturing method for a non-invasive blood glucose monitoring device which is able to offer a limiting effect for a transparent cover.

To achieve the above mentioned objectives, the manufacturing method for a non-invasive blood glucose monitoring device of the present invention comprises steps of: providing a substrate; performing an injection molding process or an electroplating process, to form at least one light-blocking wall on the substrate, wherein each light-blocking wall includes a lower wall-structure and an upper wall-structure, and the lower wall-structure connects the substrate and the upper wall-structure connects the lower wall-structure; arranging a light-emitting element and a light-receiving element on the substrate and separating the light-emitting element and the light-receiving element by the at least one light-blocking wall; forming a packaging structure on the substrate in which the light-emitting element and the light-receiving element are packaged; and disposing a transparent cover on the packaging structure and the at least one light-blocking wall and limiting the transparent cover to a configuration height by the at least one light-blocking wall.

In one embodiment of the present invention, a thermoplastic polymer material is adopted to form the at least one light-blocking wall for the injection molding process.

In one embodiment of the present invention, a metal material or an alloy material is adopted to form the at least one light-blocking wall for the electroplating process.

In one embodiment of the present invention, a width of the lower wall-structure is wider than a width of the upper wall-structure.

In one embodiment of the present invention, the width of the lower wall-structure is two to three times of the width of the upper wall-structure.

In one embodiment of the present invention, a width of the lower wall-structure is between 100 μm and 300 μm and a width of the upper wall-structure is between 50 μm and 100 μm.

In one embodiment of the present invention, a height of the upper wall-structure equals a height of the transparent cover.

In one embodiment of the present invention, the packaging structure and the lower wall-structure have the same height.

In one embodiment of the present invention, each of the light-blocking wall forms a staged and three-dimensional structure through the upper wall-structure and the lower wall-structure.

In one embodiment of the present invention, a light transmittance of each of the at least one light-blocking wall is not greater than 5%, or a light reflectance of each of the at least one light-blocking wall is not less than 95%.

The present invention also provides a non-invasive blood glucose monitoring device. The non-invasive blood glucose monitoring device comprises a substrate, at least one light-blocking wall, a light-emitting element, a light-receiving element, a packaging structure and a transparent cover. Each of the at least one light-blocking wall includes a lower wall-structure and an upper wall-structure, and the lower wall-structure connects the substrate and the upper wall-structure connects the lower wall-structure. The light-emitting element and the light-receiving element are both disposed on the substrate, and the light-emitting element and the light-receiving element are separated by the at least one light-blocking wall. The packaging structure is disposed on the substrate, in which the light-emitting element and the light-receiving element are packaged. The transparent cover is disposed on the packaging structure and the at least one light-blocking wall, and the transparent cover is limited to a configuration height by the at least one light-blocking wall.

In one embodiment of the present invention, the at least one light-blocking wall directly forms on the substrate by performing an injection molding process or an electroplating process.

For the conventional manufacturing methods of non-invasive blood glucose monitoring devices, packaging process is first proceeded, and then a cutting process for grooves and a glue dispensing process are cooperatively proceeded to form light-blocking walls. By comparison, for the manufacturing method for a non-invasive blood glucose monitoring device of the present invention, the light-blocking wall is formed on the substrate first by the three-dimensional forming process, and then the arrangement and packaging process of the light-emitting element and the light-receiving element are proceeded, so as to effectively simplify the manufacturing processes and to reduce the width of the light-blocking wall. Moreover, through the design of the stair-like and three-dimensional structure of each of the light-blocking wall, the supporting and limiting effects for the transparent cover are provided. In addition, for the light-blocking wall manufactured by the manufacturing method for a non-invasive blood glucose monitoring device of the present invention, the uniformity of the material inside is improved and the generated bubbles are reduced, thereby keeping the high light reflectance and the low light transmittance of the light-blocking wall.

DETAILED DESCRIPTION OF THE PREFERRED EMBODIMENT

Since various examples and embodiments in the present invention are only illustrative and non-restrictive, a person skilled in the art can easily conceive other examples and embodiments without contravening the scope of the present invention, after reading this specification, and can make the features and advantages of these embodiments more evident based on the following detailed description and claims.

Herein, the description of unit, element and component in the present invention uses "one", "a", or "an". This is for convenience and for offering general meaning of the category of the present invention. Therefore, the description should be understood as including "one", "at least one", and singular and plural forms at the same time unless the context clearly indicates otherwise.

Herein, the description of the terms "first" or "second" and similar ordinal numbers are mainly used to distinguish or refer to the same or similar elements or structures and do not necessarily imply that such components or structures are spatially or temporally distinct order. It should be understood that ordinal numbers, in certain situations or configurations, may be used interchangeably without affecting the implementation of the present invention.

Herein, the description of "comprise", "have" or other similar semantics have the non-exclusive meaning. For example, components or structures with a plurality of elements are not only limited to those disclosed in this specification, but also include generally inherent elements, which are not explicitly listed here for the components or the structures.

Figure 1:
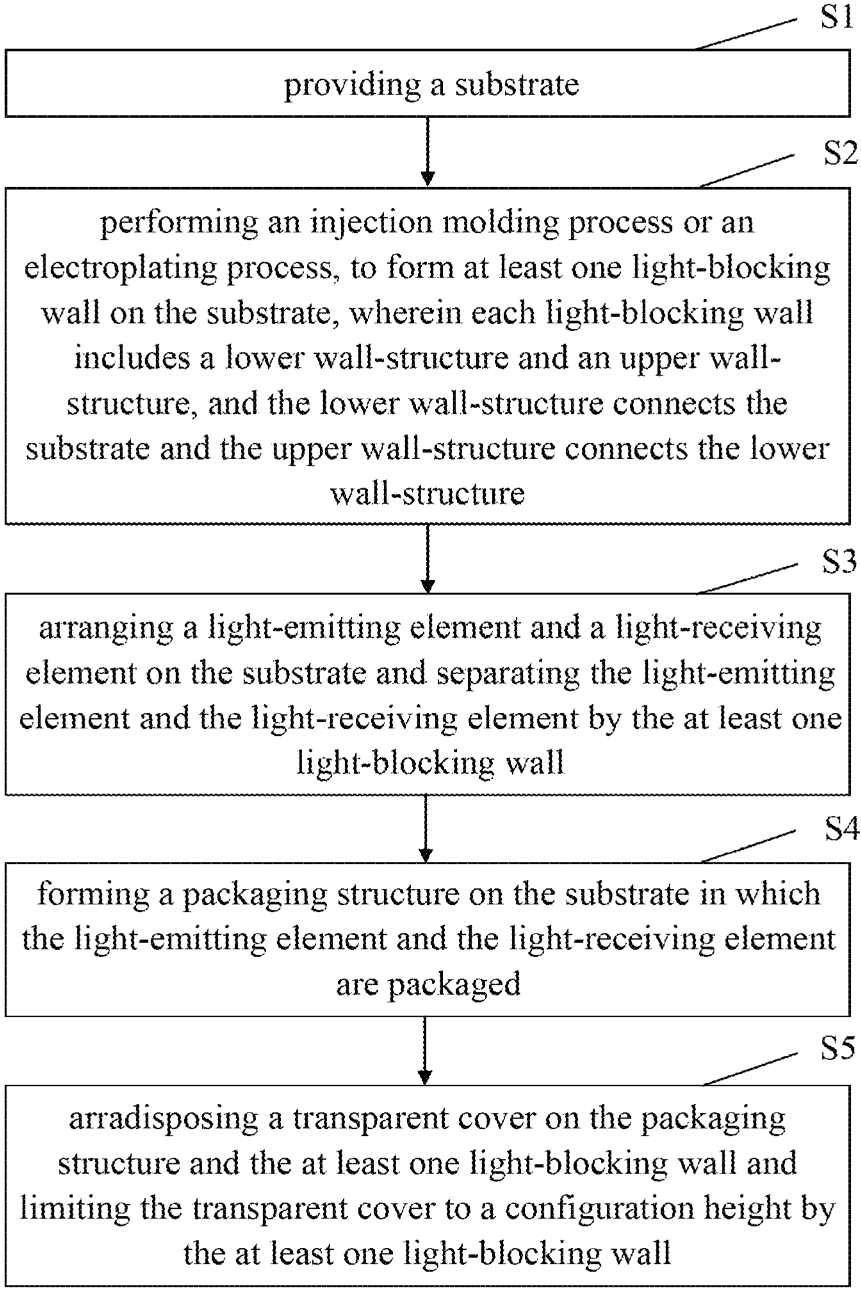
FIG. 1 is a flowchart of a manufacturing method of a non-invasive blood glucose monitoring device according to the present invention.
Figure 2:
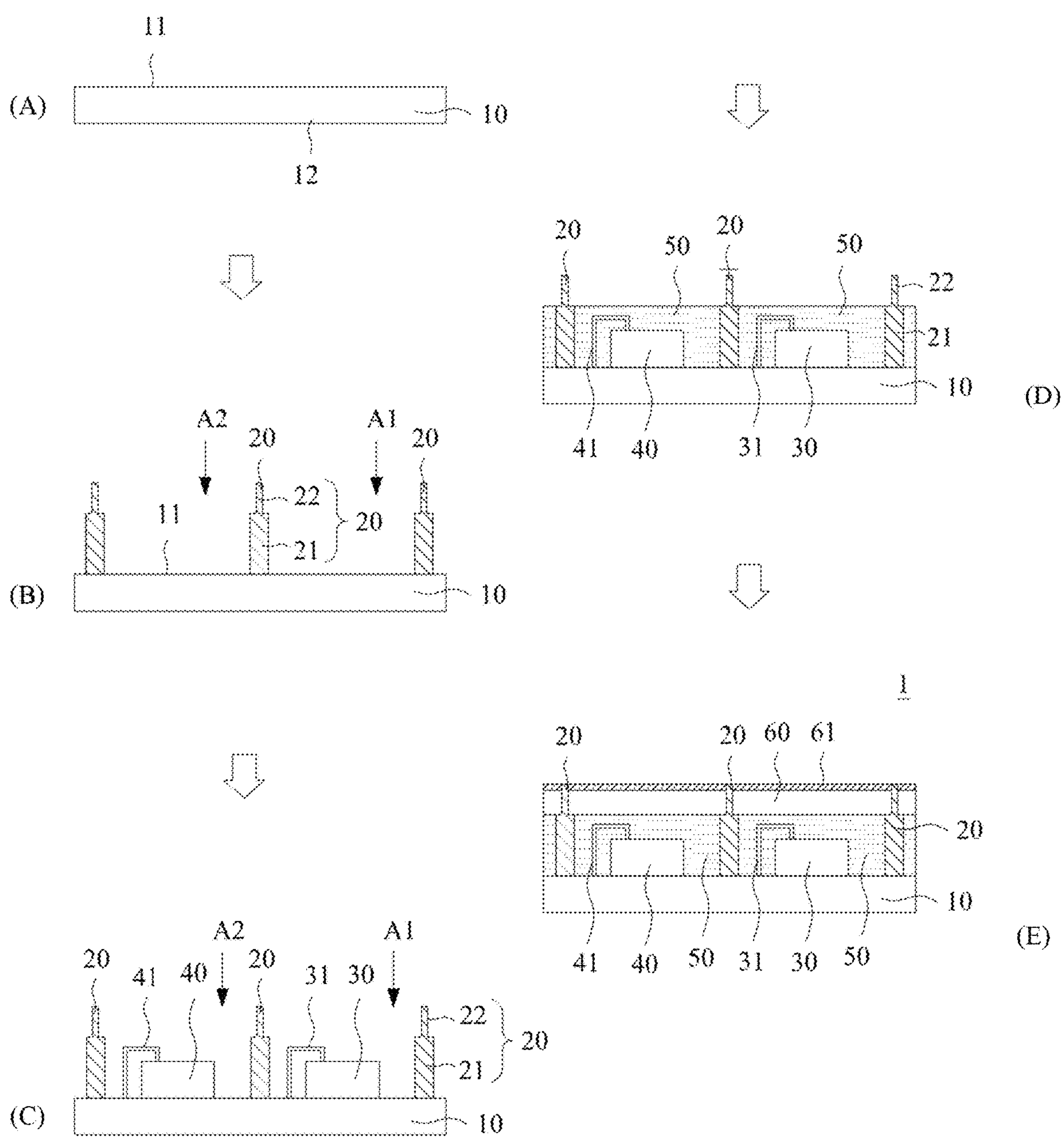
FIG. 2 is a schematic view of manufactured configurations corresponding to steps for the manufacturing method of the non-invasive blood glucose monitoring device according to the present invention.

Please refer to FIG. 1 and FIG. 2 together, wherein FIG. 1 is a flowchart of a manufacturing method of a non-invasive blood glucose monitoring device according to the present invention, and FIG. 2 is a schematic view of manufactured configurations corresponding to steps for the manufacturing method of the non-invasive blood glucose monitoring device according to the present invention. As shown in FIG. 1 and FIG. 2, the manufacturing method of the non-invasive blood glucose monitoring device according to the present invention comprises following steps (step S1 to step S5).

Step S1: providing a substrate.

First, the present invention provides a substrate 10 as a basic structure component of the non-invasive blood glucose monitoring device 1, for carrying other components of the non-invasive blood glucose monitoring device 1. The substrate 10 is a flat structure, the substrate 10 includes a first surface 11 and a second surface 12 opposite to each other, and a circuit is arranged on the substrate 10 in advance. In the present invention, the substrate 10 is a ceramic substrate, a silicon substrate or a PCB substrate, but not limited thereto. The substrate 10 can also be made of other materials.

Step S2: performing an injection molding process or an electroplating process, to form at least one light-blocking wall on the substrate, wherein each light-blocking wall includes a lower wall-structure and an upper wall-structure, and the lower wall-structure connects the substrate and the upper wall-structure connects the lower wall-structure.

After the substrate 10 is provided in the step S1, an injection molding process or an electroplating process is then performed, to directly form at least one light-blocking wall 20 on the first surface 11 of the substrate 10 for the present invention. The light-blocking wall 20 mainly provides an effect of light-blocking, so the light-blocking wall 20 is made of a lightproof (including visible light and invisible light) material. In one embodiment of the present invention, if the injection molding process is performed, a thermoplastic polymer material is adopted to form the at least one light-blocking wall. The aforementioned thermoplastic polymer material includes polystyrene, low density polyethylene, polyoxymethylene or other polymer material with a similar property, but not limited thereto. In another embodiment of the present invention, if the electroplating process is performed, a metal material or an alloy material is adopted to form the at least one light-blocking wall. The aforementioned metal material includes zinc, copper, nickel or other metal material with a similar property, and the aforementioned alloy material includes zinc-nickel alloy, bronze, brass or other alloy material with a similar property, but not limited thereto. Through the aforementioned process and the material property of the at least one light-blocking wall, a light transmittance of each light-blocking wall 20 after being formed is not greater than 5%, or a light reflectance of each light-blocking wall 20 is not less than 95%, even achieving 100% light blocking rate, so as to provide a better effect of light-blocking.

In the present invention, each of the at least one light-blocking wall 20 includes a lower wall-structure 21 and an upper wall-structure 22. One end of the lower wall-structure 21 connects the substrate 10, and the upper wall-structure 22 connects the other end of the lower wall-structure 21, so that each of the at least one light-blocking wall 20 entirely forms a stair-like and three-dimensional structure. That is to say, a width of each of the lower wall-structure 21 is wider than a width of each of the upper wall-structure 22 in the present invention. In another structural design, the width of the lower wall-structure 21 of each light-blocking wall 20 can be two to three times of the width of the upper wall-structure 22. Accordingly, in addition to that each light-blocking wall 20 has its own light-blocking effect, the lower wall-structure 21 can provide stable supporting for the light-blocking wall 20, and the upper wall-structure 22 can further extends the light-blocking effect to the transparent cover 60. And through width differences between the lower wall-structures 21 and the upper wall-structures 22, a groove-like structure can be formed to provide a limiting effect for a transparent cover 60 which is disposed subsequently. Moreover, in accordance with disposing of a packaging structure 50 and the transparent cover 60 subsequently, a height of the lower wall-structure 21 and a height of the upper wall-structure 22 can also be adjusted accordingly.

Before the injection molding process or the electroplating process is performed, a three-dimensional structure shape and a size of each light-blocking wall 20 can be set in advance. Thus, each light-blocking wall 20 is formed according to the default structure shape and the default size on the substrate 10, after the corresponding process is performed. In one embodiment of the invention, for each light-blocking wall 20, the width of the lower wall-structure 21 is between 100 μm and 300 μm and the width of the upper wall-structure 22 is between 50 μm and 100 μm. According to different design requirements, a height of each light-blocking wall 20 can also be changed.

In the present invention, numbers and positions of the at least one light-blocking wall 20 are adjusted according to different design requirements. For example, if the at least one light-blocking wall 20 is single, the light-blocking wall 20 will be disposed between light-emitting element 30 and a light-receiving element 40 described later, for preventing that light emitted from light-emitting element 30 is directly received by the light-receiving element 40. If the at least one light-blocking wall 20 is plural, the light-blocking walls 20 can be arranged around the light-emitting element 30 and the light-receiving element 40 described later, for further preventing that light sources outside the device induce interferences relative to the light-receiving element 40 and the light-emitting element 30, and for promoting that the light is concentratedly emitted or received.

Step S3: arranging a light-emitting element and a light-receiving element on the substrate and separating the light-emitting element and the light-receiving element by the at least one light-blocking wall.

As the at least one light-blocking wall 20 in the step S2 is formed, disposing of light-emitting element 30 and the light-receiving element 40 on the first surface 11 of the substrate 10 is sequentially proceeded for the present invention. The light emitting-element 30 mainly emits light in a specific wavelength band toward skins. In the present invention, a single LED light source is used for the light-emitting element 30, but the type, location and quantity of the light-emitting element 30 can be adjusted according to different design requirements. The light-emitting element 30 can be electrically connected to the substrate 10 through a bonding wire 31. The light-receiving element 40 mainly receives the light in the specific wavelength band after being diffusely reflected by the skins and then transmitting back. In the present invention, a single photo detector is applied for the light-receiving element 40, but the type, location and quantity of the light-receiving element 40 can be adjusted according to different design requirements. The light-receiving element 40 can be electrically connected to the substrate 10 through another bonding wire 41. In design, the light-emitting element 30 and the light-receiving element 40 keep a certain distance and are separated by the at least one light-blocking wall 20 to prevent that the light-receiving element 40 directly receives the light emitted by the light-emitting element 30 and thus the accuracy of monitoring results are affected.

Step S4: forming a packaging structure on the substrate in which the light-emitting element and the light-receiving element are packaged.

After the light-emitting element 30 and the light-receiving element 40 are arranged in the step S3, a packaging structure 50 in which the light-emitting element 30 and the light-receiving element 40 are packaged is formed on the substrate 10. A packaging material is previously filled on the first surface 11 of the substrate 10, to make the light-emitting element 30 and the light-receiving element 40 completely buried in the packaging material, and then compression molding is performed relative to the filled packaging material, so as to form a packaging structure 50 in which the light-emitting element 30 (may also including the bonding wire 31) and the light-receiving element 40 (may also including the bonding wire 41) are embedded. The aforementioned packaging material may be a transparent liquid optical glue or an epoxy resin, but the present invention is not limited thereto. In one embodiment of the present invention, a height of the formed packaging structure 50 is more than a height of the light-emitting element 30 and a height of the light-receiving element 40, so as to reserve a space for disposing of the bonding wire 31 or 41. On the other hand, the packaging structure 50 has the same height as that of the lower wall-structure 21 of each light-blocking wall 20 to facilitate the subsequent setting of the transparent cover 60.

For example, in one embodiment of the present invention, the at least one light-blocking wall 20 is plural, and a first space A1 and a second space A2 isolated from each other are formed on the substrate 10 through those light-blocking walls 20. The light-emitting element 30 is located in the first space A1, and the light-receiving element 40 is located in the second space A2. Therefore, the packaging material can be filled into the first space A1 and the second space A2 to form the packaging structure 50 in which the light-emitting element 30, bonding wire 31, the light-receiving element 40 and bonding wire 41 are embedded.

Step S5: disposing a transparent cover on the packaging structure and the at least one light-blocking wall and limiting the transparent cover to a configuration height by the at least one light-blocking wall.

As the packaging structure 50 is formed in the step S4, a transparent cover 60 is then fixedly set on the packaging structure 50 and the at least one light-blocking wall 20 for the present invention. The transparent cover 60 mainly provides a protection effect for other components of the non-invasive blood glucose monitoring device 1. The transparent cover 60 is made of a transparent material, such as glass, but the invention is not limited thereto. The transparent cover 60 can be fixed on the packaging structure 50 and the at least one light-blocking wall 20 by gluing. Since the packaging material forming the packaging structure 50 itself has an adhesive force, an adhesively fixing effect on the transparent cover 60 occurs by the packaging material when the transparent cover 60 is set. In one embodiment of the present invention, the height of the upper wall-structure 22 equals a height of the transparent cover 60. Therefore, the groove formed by the width difference between the lower wall-structure 21 and the upper wall-structure 22 of each light-blocking wall 20 can be used as a limiting structure for setting the transparent cover 60, so that the transparent cover 60 can be kept at a configuration height and will not downward compress or contact with the bonding wires 31 or 41. For example, a thickness of the transparent cover 60 is between 50 μm and 500 μm according to different designs. Hence, the height of the upper wall-structure 22 of each light-blocking wall 20 can also be adjusted to be between 50 μm and 500 μm in accordance with the thickness design of the transparent cover 60, but the present invention is not limited thereto.

The transparent cover 60 further includes a coating 61, and the coating 61 is formed on a side of the transparent cover 60 facing away from the substrate 10. Through the arrangement of the coating 61, the transparent cover 60 can provide an effect for allowing light in a specific wavelength band to pass through, and can effectively block stray light in other unnecessary wavelength band. Since the coating 61 is a structural design often used for conventional transparent covers, no further details) will be given here.

In the manufacturing method for the non-invasive blood glucose monitoring device of the present invention, the at least one light-blocking wall 20 with a default structure shape and a default size is first formed on the substrate 10 through the injection molding process or the electroplating process, then the arrangement and the packaging process of the light-emitting element 30 and the light-receiving element 40 is proceeded, and at last the transparent cover 60 is disposed and cutting operations are proceeded according to the design requirements, so that the non-invasive blood glucose monitoring device 1 of the present invention can be manufactured. Compared with the conventional manufacturing methods of non-invasive blood glucose monitoring devices, the manufacturing method of the non-invasive blood glucose monitoring device of the present invention simplifies the overall manufacturing processes and is able to cope with large-area production (for example, the manufacturing area can be increased to more than 2 square inches), through changing processes which comprise packaging the components for half-cutting to form grooves previously and forming a light-blocking wall then by dispensing.

Furthermore, the manufacturing method of the non-invasive blood glucose monitoring device of the present invention is able to form the at least one light-blocking wall 20 with a default size according to design requirements, and the width of each light-blocking wall 20 can be reduced to less than 100 μm, without being subject to sizes of cutting tools. Compared to the conventional manufacturing methods of non-invasive blood glucose monitoring devices, the width of each light-blocking wall 20 can be significantly reduced. On the other hand, for the light-blocking wall 20 formed by the injection molding process or the electroplating process, bubbles are not easily generated during the process, and uniformity of the material inside the light-blocking wall 20 can be effectively improved, thereby keeping the high light reflectance and the low light transmittance of the light-blocking wall 20. Moreover, the light-blocking wall 20 adopts a staged and three-dimensional structure design, which can effectively provide supporting and limiting effects for the transparent cover 60, so as to limit the configuration height of the transparent cover 60. Accordingly, the overall configuration of the non-invasive blood glucose monitoring device 1 of the present invention can be miniaturized and its application flexibility is improved.

Figure 3:
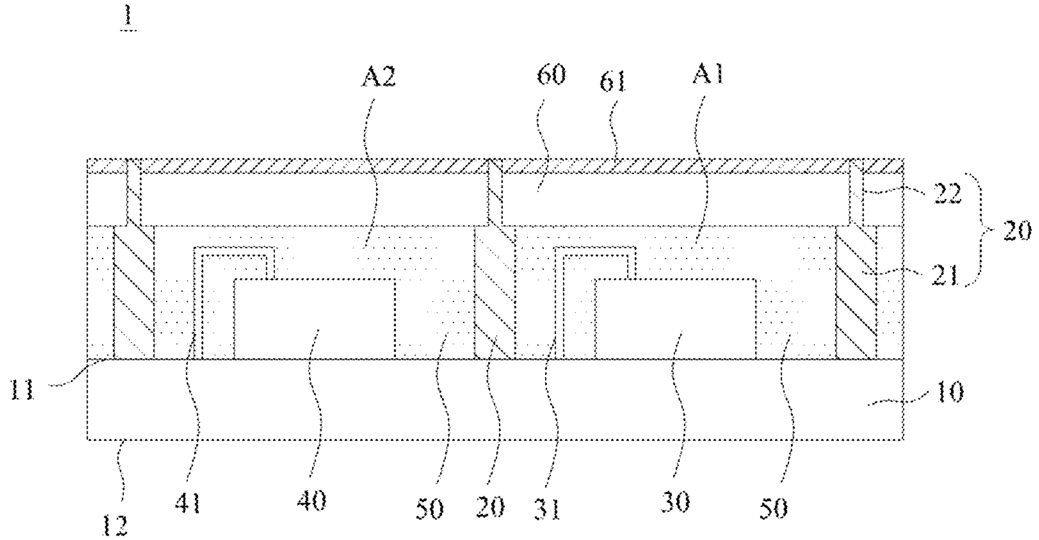
FIG. 3 is a schematic view of the non-invasive blood glucose monitoring device produced by the manufacturing method of a non-invasive blood glucose monitoring device according to the present invention.

Please refer to FIG. 1 to FIG. 3 together. FIG. 3 is a schematic view of the non-invasive blood glucose monitoring device produced by the manufacturing method of a non-invasive blood glucose monitoring device according to the present invention. As shown in FIG. 1 to FIG. 3, the present invention also discloses the non-invasive blood glucose monitoring device 1 produced by the aforementioned manufacturing method of the non-invasive blood glucose monitoring device. The non-invasive blood glucose monitoring device 1 of the present invention mainly comprises the substrate 10, the at least one light-blocking wall 20, the light-emitting element 30, the light-receiving element 40, the packaging structure 50 and the transparent cover 60. Since each of the aforementioned structural elements and their functions have been described in the foregoing content, no further details will be described here.

The above implementations are only auxiliary descriptions, and are not intended to limit the embodiments of the application subject or the applications or uses of the embodiments. In addition, although at least one illustrative example has been presented above, it should be understood that the present invention can still have a large number of variations. It should also be understood that the embodiments described herein are not intended to limit the scope, use, or configuration of the requested subject matter in any way. On the contrary, the foregoing embodiments will provide a convenient guide for those skilled in the art to implement one or more embodiments. Furthermore, various changes can be made to the function and arrangement of the components without departing from the scope defined by the patent claims, and the scope of the patent claims includes known equivalents and all foreseeable equivalents at the time that the patent application is filed.

What is claimed is:

1. A manufacturing method for a non-invasive blood glucose monitoring device, comprising steps of:

providing a substrate, performing an injection molding process or an electroplating process, to form at least one light-blocking wall on the substrate, wherein each light-blocking wall includes a lower wall-structure and an upper wall-structure, and the lower wall-structure connects the substrate and the upper wall-structure connects the lower wall-structure, arranging a light-emitting element and a light-receiving element on the substrate and separating the light-emitting element and the light-receiving element by the at least one light-blocking wall, forming a packaging structure on the substrate in which the light-emitting element and the light-receiving element are packaged, and disposing a transparent cover on the packaging structure and the at least one light-blocking wall and limiting the transparent cover to a configuration height by the at least one light-blocking wall, wherein a width of the lower wall-structure is wider than a width of the upper wall-structure, so that a limit structure for setting the transparent cover is formed by a width difference between the lower wall-structure and the upper wall-structure, and a height of the upper wall-structure equals a height of the transparent cover.

2. The manufacturing method for a non-invasive blood glucose monitoring device as claimed in claim 1, wherein a thermoplastic polymer material is adopted to form the at least one light-blocking wall for the injection molding process.

3. The manufacturing method for a non-invasive blood glucose monitoring device as claimed in claim 1, wherein a metal material or an alloy material is adopted to form the at least one light-blocking wall for the electroplating process.

4. The manufacturing method for a non-invasive blood glucose monitoring device as claimed in claim 1, wherein the width of the lower wall-structure is two to three times of the width of the upper wall-structure.

5. The manufacturing method for a non-invasive blood glucose monitoring device as claimed in claim 1, wherein a width of the lower wall-structure is between 100 μm and 300 μm and a width of the upper wall-structure is between 50 μm and 100 μm.

6. The manufacturing method for a non-invasive blood glucose monitoring device as claimed in claim 1, wherein the packaging structure and the lower wall-structure have the same height.

7. The manufacturing method for a non-invasive blood glucose monitoring device as claimed in claim 1, wherein each of the light-blocking wall forms a staged and three-dimensional structure through the upper wall-structure and the lower wall-structure.

8. The manufacturing method for a non-invasive blood glucose monitoring device as claimed in claim 1, wherein a light transmittance of each of the at least one light-blocking wall is not greater than 5%, or a light reflectance of each of the at least one light-blocking wall is not less than 95%.

* * * * *